United States Patent
Srinivasan

(10) Patent No.: US 9,133,441 B2
(45) Date of Patent: Sep. 15, 2015

(54) ENHANCING A POPULATION OF INSULIN RELEASING CELLS USING GFR α-1 AGONISTS

(71) Applicant: Shanthi Srinivasan, Atlanta, GA (US)

(72) Inventor: Shanthi Srinivasan, Atlanta, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 0 days.

(21) Appl. No.: 14/108,531

(22) Filed: Dec. 17, 2013

(65) Prior Publication Data

US 2014/0186949 A1    Jul. 3, 2014

Related U.S. Application Data

(62) Division of application No. 11/936,413, filed on Nov. 7, 2007, now Pat. No. 8,637,459.

(60) Provisional application No. 60/857,703, filed on Nov. 8, 2006.

(51) Int. Cl.
  *A61K 38/00* (2006.01)
  *C12N 5/071* (2010.01)
  *A61K 38/18* (2006.01)
  *A61K 35/12* (2015.01)

(52) U.S. Cl.
  CPC ............ *C12N 5/0676* (2013.01); *A61K 38/185* (2013.01); *A01K 2267/0362* (2013.01); *A61K 35/12* (2013.01); *C12N 2501/13* (2013.01)

(58) Field of Classification Search
  CPC . C12N 5/0676; C12N 2501/13; A61K 38/185
  USPC ............................................. 514/6.7, 6.8, 6.9
  See application file for complete search history.

(56) References Cited

U.S. PATENT DOCUMENTS

| | | | |
|---|---|---|---|
| 6,221,376 B1 | 4/2001 | Lin et al. | |
| 6,391,312 B1 | 5/2002 | Kishino et al. | |
| 6,866,851 B1 | 3/2005 | Milbrandt et al. | |
| 8,399,408 B2 * | 3/2013 | Austen et al. | 514/6.8 |
| 8,637,459 B2 | 1/2014 | Srinivasan | |

FOREIGN PATENT DOCUMENTS

EP    0045665    2/1982

OTHER PUBLICATIONS

Rossi et al. Diabetes 2005;54:1324-30.*
Neurturin, NCBI, Mesh term database 2006.*
Yoon et al. Glial cell-line derived neurotrophic factor and neurturin regulate the expressions of distinct miRNA precursors through the activation of GFRa2, J Neurochemistry, 2006, 98, 1149-1158.
Sutherland et al. Pancreas transplantation in nonuremic, type I diabetic recipients, Surgery, 1988, 453.
Sima & Kamiya Diabetic Neuropathy Differs in Type 1 and Type 2 Diabetes Ann. N.Y. Acad. Sci. 1084: 235-249 (2006).
Nishikiori et al. Glial Cell Line-Derived Neurotrophic Factor in the Vitreous of Patients With Proliferative Diabetic Retinopathy, Diabetes Care, vol. 28, No. 10, 2005, 2588.
Mwangi et al., Glial Cell Line-Derived Neurotrophic Factor Increases Beta-Cell Mass and Improves Glucose Tolerance, Gastroenterology 2008;134:727-737.
Mwangi et al., Glial cell line-denved neurotrophic factor enhances neurogenin3 gene expression and beta-cell proliferation in the developing mouse pancreas Am J Physiol Gastrointest Liver Physiol 299: G283-G292, 2010.
Christianson et al., Restorative effects of neurotrophin treatment on diabetes-induced cutaneous axon loss in mice Experimental Neurology 179 (2003) 188-199.
Anitha et al., GDNF rescues hyperglycemia-induced diabetic enteric neuropathy through activation of the PI3K/Akt pathway J. Clin. Invest. 116:344-356 (2006).
Eketjall et al, "Distinct structural elements in GDNF mediate binding to GRFα1 and activation of the GFRα1-c-Ret receptor complex," The EMBO Journal, 18(21):5901-5910 (1999).
Bespalov & Saarma GDNF family receptor complexes are emerging drug targets, Trends in Pharmacological Sciences vol. 28 No. 2, 68.
Mwangi at al., "Transgenic mice over expressing Glial Derived Neurotrophic Factor have increased beta cell mass," Poster, FASEBJ., 21:924.5 (2007).

* cited by examiner

*Primary Examiner* — Janice Li
(74) *Attorney, Agent, or Firm* — Emory Patent Group

(57) ABSTRACT

Provided herein are pharmaceutical and transplant compositions and methods related to the treatment and prevention of diabetes. More specifically, the compositions and methods are related to activation of glial derived neurotrophic factor (GDNF) receptors or overexpression of the GFR-α1/c-Ret receptor complex in insulin secreting cells so as to promote cell survival and proliferation.

10 Claims, 12 Drawing Sheets

Fig. 1
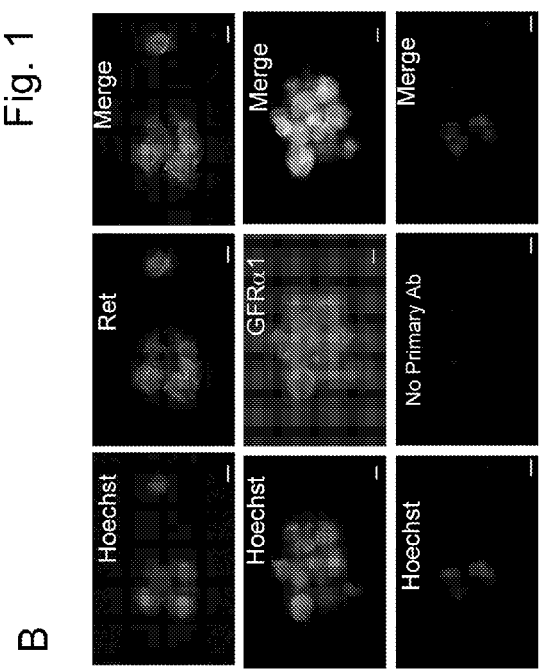
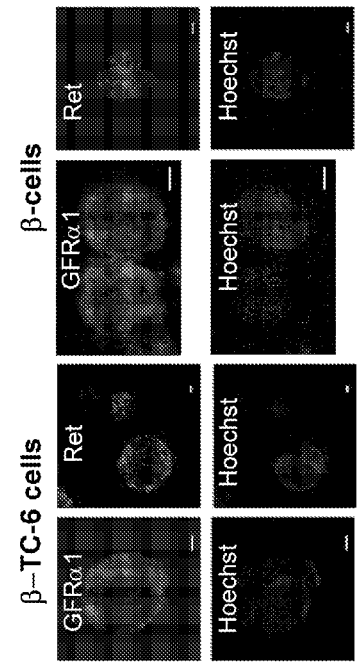
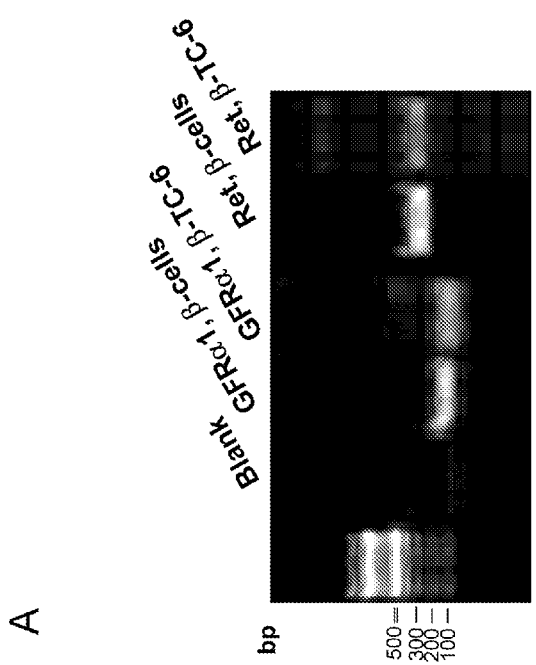
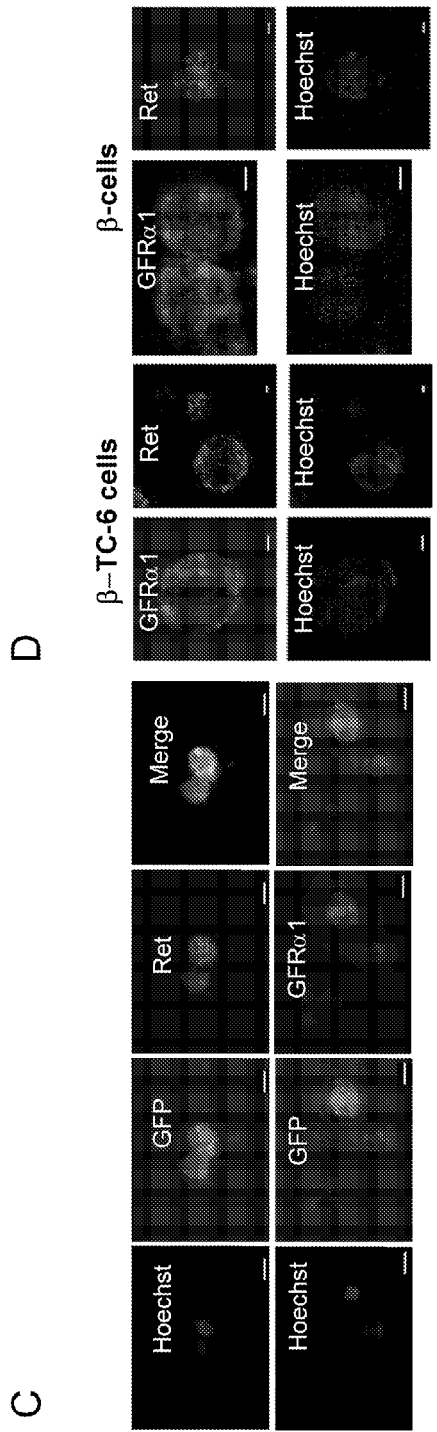

Fig. 3
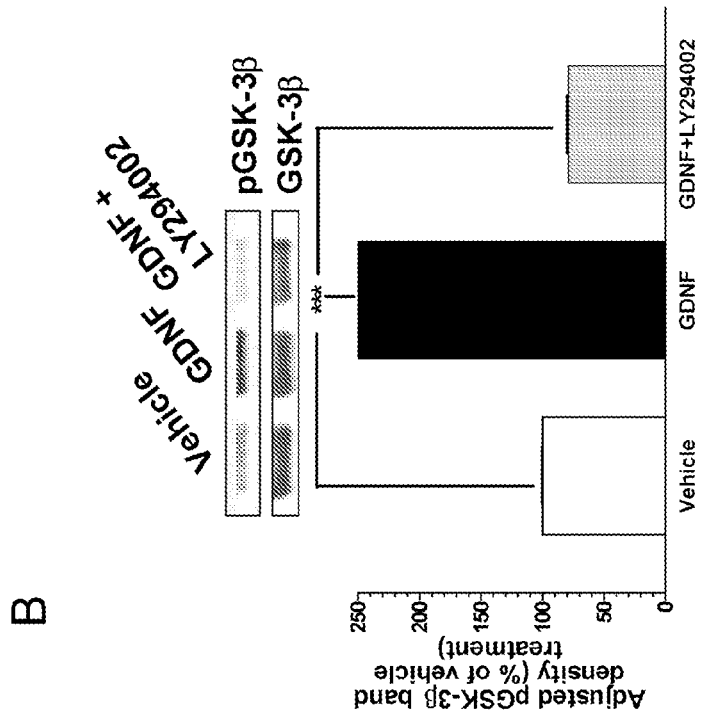
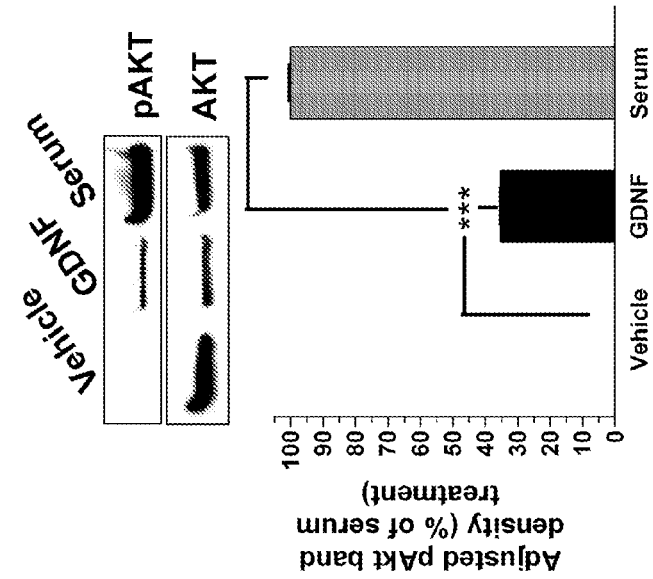

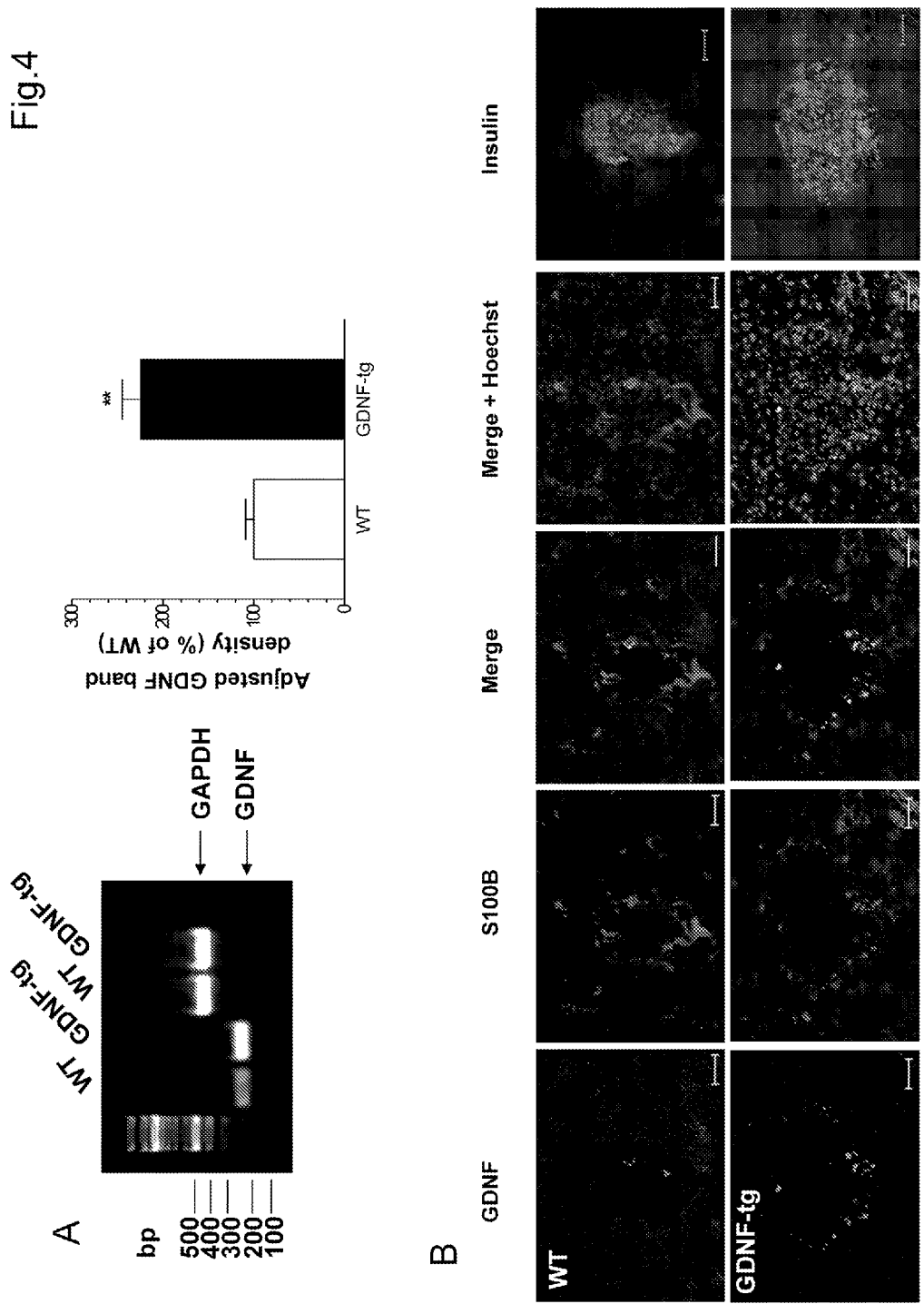

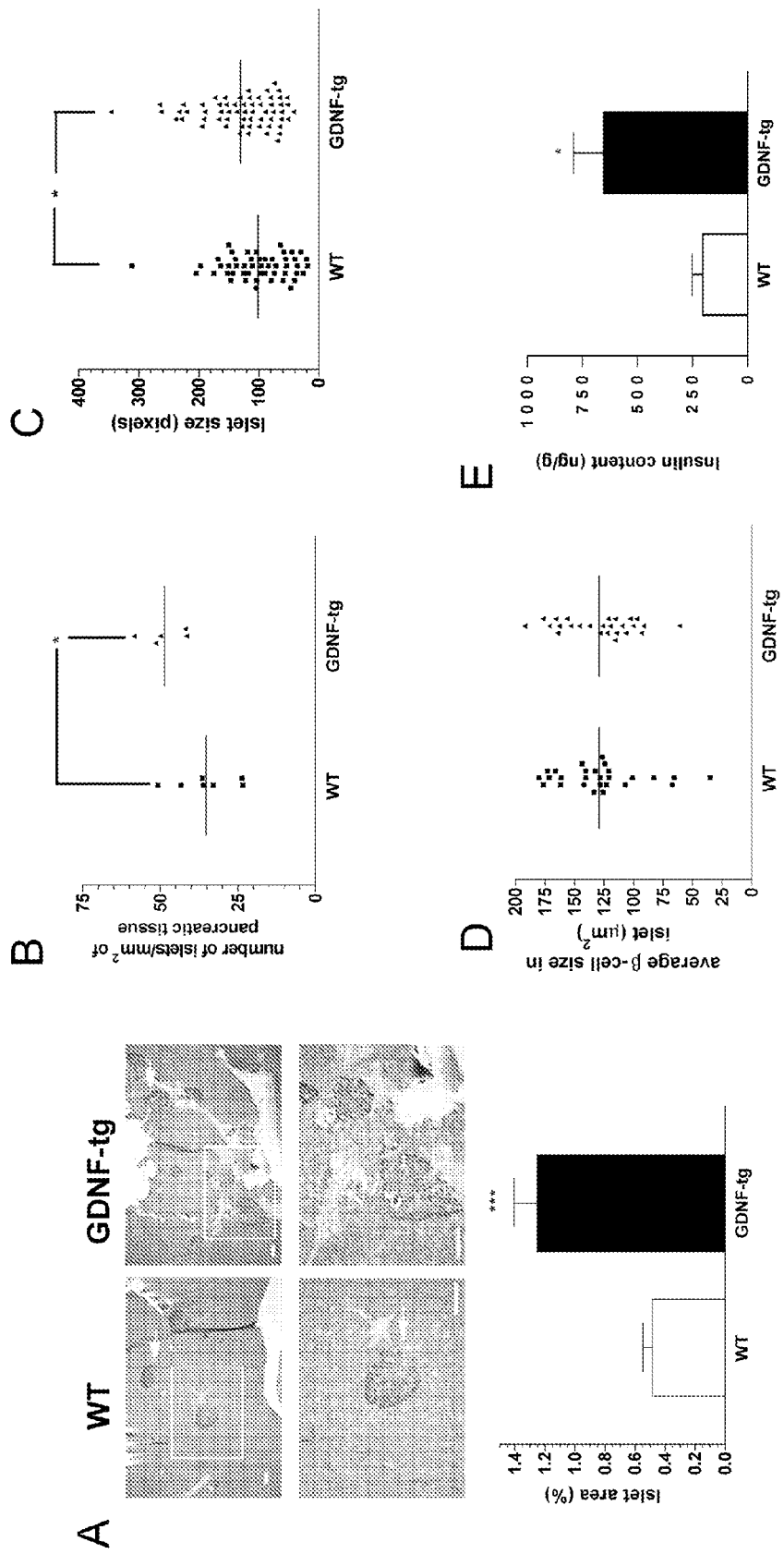

Fig. 6
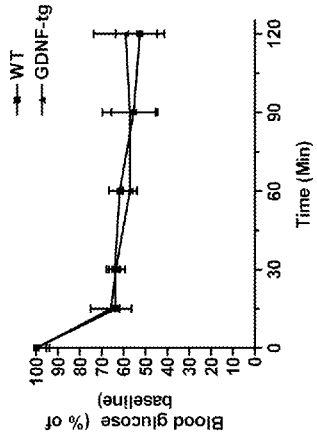
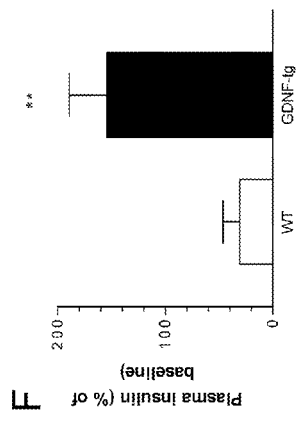
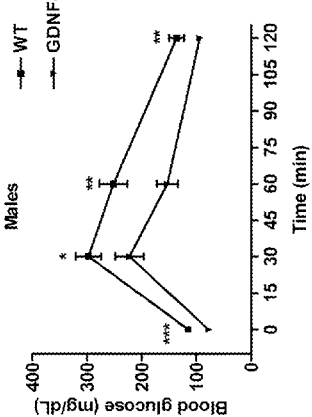
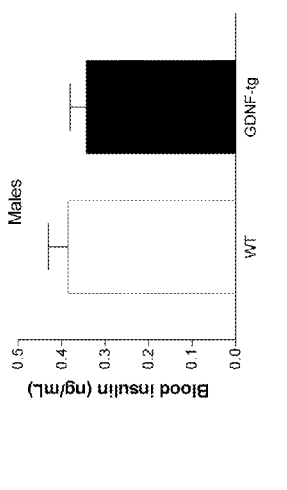
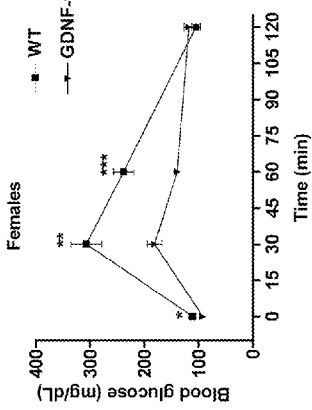
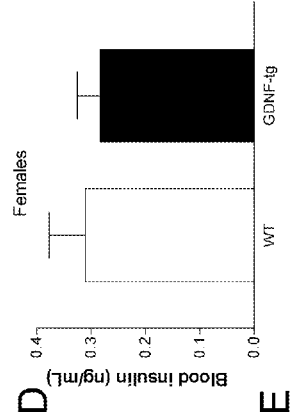

Fig. 8
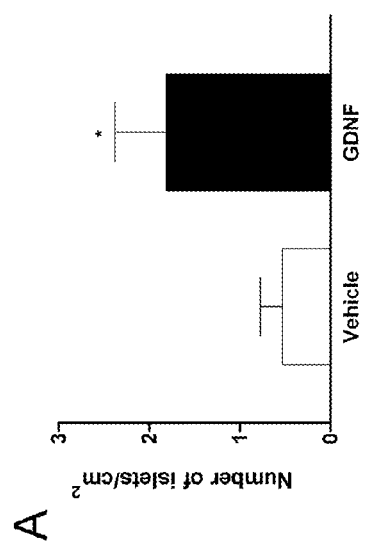
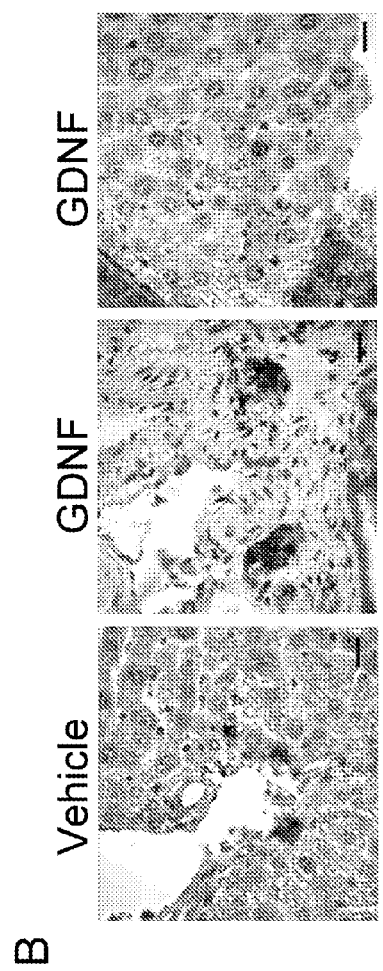

```
SEQUENCE LISTING

<160> NUMBER OF SEQ ID NOS: 9

<210> SEQ ID NO 1
<211> LENGTH: 18
<212> TYPE: DNA
<213> ORGANISM: Artificial Sequence
<220> FEATURE:
<223> OTHER INFORMATION: Synthetic constructs

<400> SEQUENCE: 1
agacgcatca cctccgct                                                       18

<210> SEQ ID NO 2
<211> LENGTH: 22
<212> TYPE: DNA
<213> ORGANISM: Artificial Sequence
<220> FEATURE:
<223> OTHER INFORMATION: Synthetic constructs

<400> SEQUENCE: 2
tgacgtcatc aaactggtca gg                                                  22

<210> SEQ ID NO 3
<211> LENGTH: 22
<212> TYPE: DNA
<213> ORGANISM: Artificial Sequence
<220> FEATURE:
<223> OTHER INFORMATION: mouse GFR alpha 1 primer

<400> SEQUENCE: 3
atgaagaacg agagaggccc aa                                                  22

<210> SEQ ID NO 4
<211> LENGTH: 22
<212> TYPE: DNA
<213> ORGANISM: Artificial Sequence
<220> FEATURE:
<223> OTHER INFORMATION: mouse GFR alpha 1 primer

<400> SEQUENCE: 4
actctggctg gcagttggta aa                                                  22

<210> SEQ ID NO 5
<211> LENGTH: 24
<212> TYPE: DNA
<213> ORGANISM: Artificial Sequence
<220> FEATURE:
<223> OTHER INFORMATION: mouse GFR alpha 1 primer

<400> SEQUENCE: 5
taccgtacac ggctgcatga gaat                                                24
```

<210> SEQ ID NO 6
<211> LENGTH: 24
<212> TYPE: DNA
<213> ORGANISM: Artificial Sequence
<220> FEATURE:
<223> OTHER INFORMATION: mouse GFR alpha 1 primer

<400> SEQUENCE: 6
atgtggaagt ggtagaaggt gcca                                          24

<210> SEQ ID NO 7
<211> LENGTH: 22
<212> TYPE: DNA
<213> ORGANISM: Artificial Sequence
<220> FEATURE:
<223> OTHER INFORMATION: mouse GFR alpha 1 primer

<400> SEQUENCE: 7
tcgatattgc agcggttcct gt                                            22

<210> SEQ ID NO 8
<211> LENGTH: 22
<212> TYPE: DNA
<213> ORGANISM: Artificial Sequence
<220> FEATURE:
<223> OTHER INFORMATION: mouse GFR alpha 1 primer

<400> SEQUENCE: 8
acatccacac cgtttagcgg aa                                            22

<210> SEQ ID NO 9
<211> LENGTH: 211
<212> TYPE: PRT
<213> ORGANISM: Artificial Sequence
<220> FEATURE:
<223> OTHER INFORMATION: synthetic peptide

<400> SEQUENCE: 9

Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Arg Ala Pro Phe Ala Leu Ser
        35                  40                  45

Ser Asp Ser Asn Met Pro Glu Asp Tyr Pro Asp Gln Phe Asp Asp Val
    50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Asp Leu Ser Phe Leu Asp

-continued

```
                180             185             190
Asp Asn Leu Val Tyr His Ile Leu Arg Lys His Ser Ala Lys Arg Cys
        195                 200                 205

Gly Cys Ile
    210
```

ENHANCING A POPULATION OF INSULIN RELEASING CELLS USING GFR α-1 AGONISTS

CROSS-REFERENCE TO RELATED APPLICATIONS

This application is a Divisional of U.S. application Ser. No. 11/936,413 filed Nov. 7, 2007, now U.S. Pat. No. 8,637,459, which claims the benefit of priority to U.S. Provisional Application No. 60/857,703 filed Nov. 8, 2006, which applications are hereby incorporated by this reference in their entireties

STATEMENT REGARDING FEDERALLY SPONSORED RESEARCH

This invention was made with government support under Grant Nos. K08-DK067045, DK075391, DK06411, and DK064399 awarded by the National Institutes of Health. The government has certain rights in the invention.

BACKGROUND

Type 1 and type 2 diabetes are characterized by loss and dysfunction of beta cells. Type 2 diabetes, which is the most common form, is associated with a gradual decline in sensitivity to insulin. Type 1 diabetes is a condition in which the body's immune cells attack 0 cells located in pancreatic islets, reducing or eliminating the body's ability to produce insulin. Treatment for type 1 diabetes is a lifelong commitment of monitoring blood glucose, exercising, dieting, and taking insulin. In some cases, individuals with type 2 diabetes similarly require insulin therapy. However, these approaches are sometimes insufficient to control blood glucose levels. Poorly controlled diabetes can lead to potentially fatal complications. Eyes, nerves and kidneys are particularly susceptible to the damage caused by poorly controlled type 1 or type 2 diabetes.

Recently great strides have been made in developing human islet transplantation in the treatment of diabetes. The lack of suitable donor pancreases is a major obstacle in the widespread use of islet cell transplants. Furthermore, this strategy faces limitations due to the large number of islets required to achieve long-term insulin independence. Often, two or far more donor organs are needed to accumulate enough islet cells for a single complete transplant. The islets are often severely injured from storage conditions or transport time causing apoptosis of the insulin secreting β-cells.

SUMMARY

Provided herein are pharmaceutical and transplant compositions and methods related to the treatment and prevention of diabetes. More specifically, the compositions and methods are related to activation of glial derived neurotrophic factor (GDNF) receptors or overexpression of the GFR-α1/c-Ret receptor complex in insulin secreting cells so as to promote cell survival and proliferation. Provided are in vitro methods for preparing or enhancing a population of insulin secreting cells for transplantation. Methods of treating diabetes in a subject and of preventing diabetes in a subject at risk are also provided. Such methods include administering a GDNF receptor agonist and/or transplanting a population of insulin secreting cells a composition of cells to the subject (e.g., a composition of glial cells and insulin secreting cells, a composition of insulin secreted cells contacted with a GDNF receptor agonist, or a composition of genetically modified cells).

DESCRIPTION OF DRAWINGS

FIG. 1 also shows laser confocal microscopy images of β-TC-6 cells and mouse pancreatic β-cells stained with anti-GFRα1 and Ret antibodies (FIG. 1D). Scale bar: 2 μm.

FIG. 2A shows Western blot analysis of cleaved caspase-3 in β-TC-6 cells cultured for 72 h in the presence of vehicle or GDNF and histogram comparison of the relative band densities. Plotted are means+SE. FIG. 2B shows immunofluorescence staining for cleaved caspase-3 and Hoechst (nuclear) in β-TC-6 cells exposed for 48 h to vehicle or GDNF and a histogram showing the percentage of apoptosis. FIG. 2C shows immunofluorescence staining for cleaved caspase-3 and Hoechst nuclear staining in β-TC-6 cells exposed for 24 h to thapsigargin (0.1 μM) in the presence of vehicle or GDNF. Scale bar, 20 μm. Histogram shows the rates of apoptosis. FIG. 2D shows a histogram with the rate of apoptosis in isolated MIP-GFP pancreatic β-cells cultured for 24 h in the presence of vehicle or GDNF (100-500 ng/ml) (mean+SE, ***, P<0.001). Data are representative of four independent experiments. FIG. 2E shows an assessment of proliferation by fluorescent staining for Ki67 in β-TC-6 cells cultured for 24 h in the presence of 10% serum with or without GDNF. Cell nuclei were counterstained with DAPI. Scale bar, 20 μm. Histogram shows the percentages of Ki67 positive cells (mean+SE *, P<0.05; **, P<0.01). Data are representative of four independent experiments.

FIG. 3A shows a Western blot analysis of Akt phosphorylation (ser473) in β-TC-6 cells treated with vehicle, GDNF (100 ng/ml) or fetal bovine serum for 30 min. Total Akt was assessed to control for protein loading. Histogram shows relative phospho-Akt (pAkt) band densities (mean+SE) adjusted for protein loading and expressed as a percentage of that of cells treated with serum. FIG. 3B shows a Western blot analysis of GSK3β (ser9) phosphorylation and total GSK3β in β-TC-6 cells treated for 30 min with vehicle, GDNF (100 ng/ml) or GDNF plus the PI3K inhibitor LY294002 (50 μM). Histogram shows relative phospho-GSK3β band densities adjusted for protein loading to total GSK3☐ staining and expressed as a percentage of that of cells treated with vehicle (mean+S.E, ***, P<0.001). Data are representative of four independent experiments.

FIG. 4 shows that GDNF-tg mice have increased GDNF expression in the islets using RT-PCR (A) and immunofluorescence (B). FIG. 4A shows RT-PCR analysis of GDNF mRNA expression in pancreata from WT and GDNF-tg mice. Glyceraldehyde-3-phosphate dehydrogenase (GAPDH) mRNA expression shows equal mRNA loading. Histogram shows relative GDNF PCR band densities. (**, P<0.01). FIG. 4B shows immunofluorescent staining of pancreas sections from WT and GDNF-tg mice showing co-localization of GDNF with S100β. Cell nuclei are stained with Hoechst. Insulin staining in the same islet from an adjacent section is shown. Scale bar 20 μm.

FIG. 5A is a photomicrographs of pancreatic sections from WT and GDNF-tg mice stained for insulin (dark) and counterstained with hematoxylin (light). Images in the lower panel are higher magnifications of the islets in the upper panel. Arrows show representative islets. Scale bar: 100 μm. Histogram shows comparison of β-cell mass (expressed as percentage insulin stained area/pancreatic area) between WT and GDNF-tg mice (means+SE, ***, P<0.001). Also shown are scatterplots of the number of islets per unit pancreatic tissue area in WT and GDNF-tg mice (FIG. 5B), of the islet size of WT and GDNF-tg mice (FIG. 5C), and of β-cell sizes between WT and GDNF-tg mice (FIG. 5D) (n=26, P>0.05). FIG. 5E shows a graph of the total insulin content of pancreata from WT and GDNF-tg mice (male and female, n=6, * P<0.05). FIG. 5F shows a histogram indicating the percentage of Ki67+β-cells (mean+SE, ***, p<0.001) in pancreatic sections from WT and GDNF-tg mice immunostained for Ki67, insulin and DAPI nuclear stain to show the presence of proliferating β-cells within islets.

FIG. 6 shows that GDNF transgenic mice have improved glucose tolerance. Eight week-old mice were fasted for 6 hour, injected intraperitoneally with glucose (2 mg/g body weight), tail blood samples taken at indicated time points, and blood glucose levels measured. Data represent plasma glucose levels of female (FIG. 6A) and male (FIG. 6B) WT and GDNF-tg mice (Mean+SE, * P<0.001; , P<0.01; *, P<0.05; females, n=6 in each group; males n=8 in each group). FIG. 6C shows a graph of blood glucose levels (mean±SE) expressed as a percentage of baseline at noted time points after insulin injection (n=4). Histograms of fasting (mean+SE) plasma c-peptide (FIG. 6D) and insulin levels (FIG. 6E) of WT and GDNF-tg mice (male and female, n=8) are also shown. FIG. 6F shows a histogram of glucose-induced insulin release for WT and GDNF-tg animals (t=2.5 min), *p<0.001, n=4 in each group.

FIG. 8 shows a histogram (FIG. 8A) of the number of vehicle and GDNF-treated islets observed per cm² of liver tissue 24 h after intrahepatic transplantation with 200 islets (Scale bar, 20 μm, n=8, *P<0.05) and representative brightfield photomicrograph images showing transplanted islets (FIG. 8B).

Unless indicated otherwise, like reference symbols in the various drawings indicate like elements.

DETAILED DESCRIPTION

Figures 1, 2:
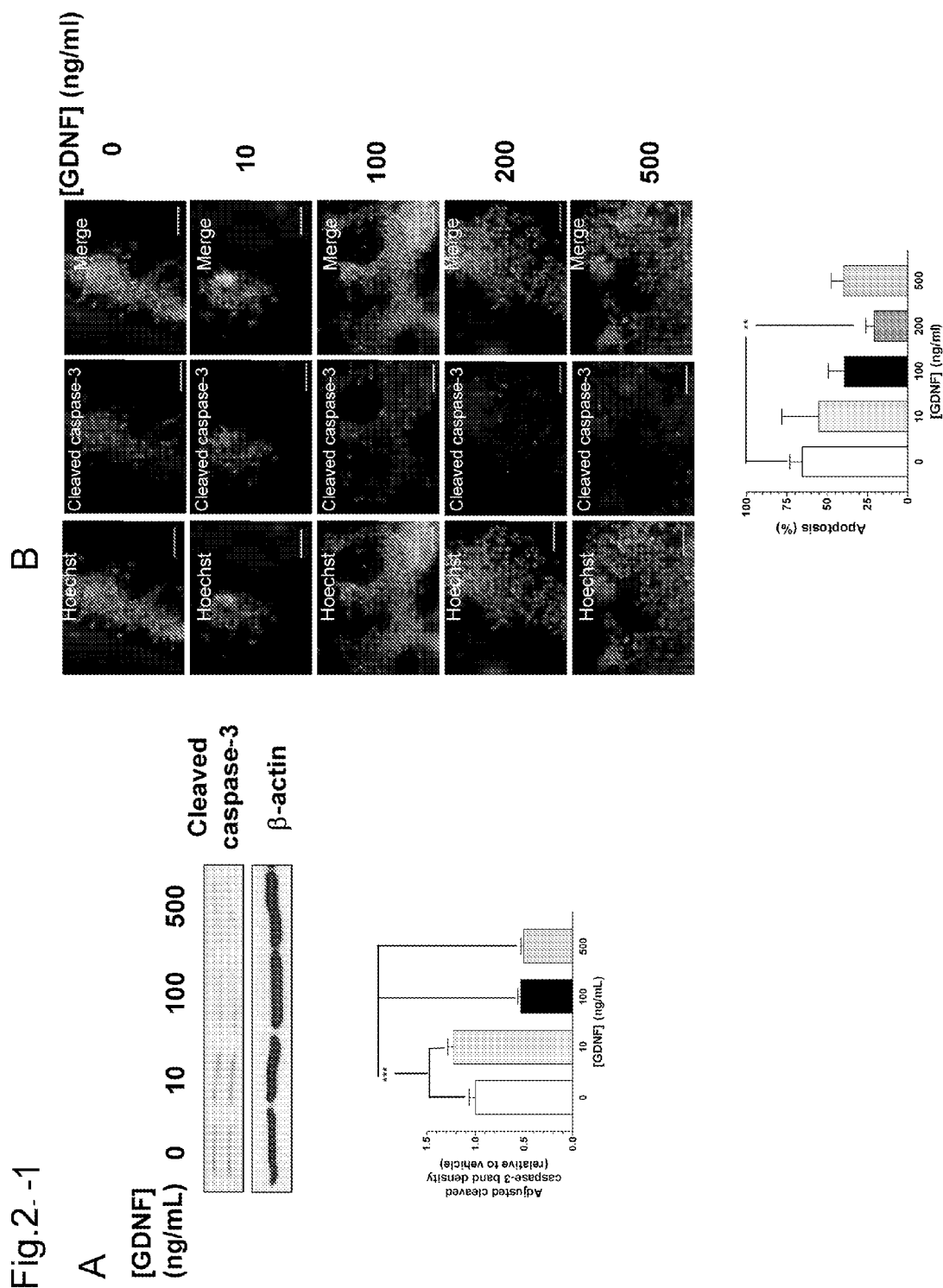
FIG. 1 shows GFRα1 and Ret receptors expression using RT-PCR analysis of GFRα1 and Ret receptor mRNA expression in the β-TC-6 cell line and mouse pancreatic β-cells (FIG. 1A) and immunofluorescence staining for GFRα1 and Ret receptors in β-TC-6 cells (FIG. 1B) and pancreatic cells isolated from MIP-GFP mice (FIG. 1C). Scale bar, 10 μm. Cell nuclei were labeled with the nuclear stain Hoechst.
FIG. 2 shows the effect of GDNF on β-cell survival.
Figure 2:
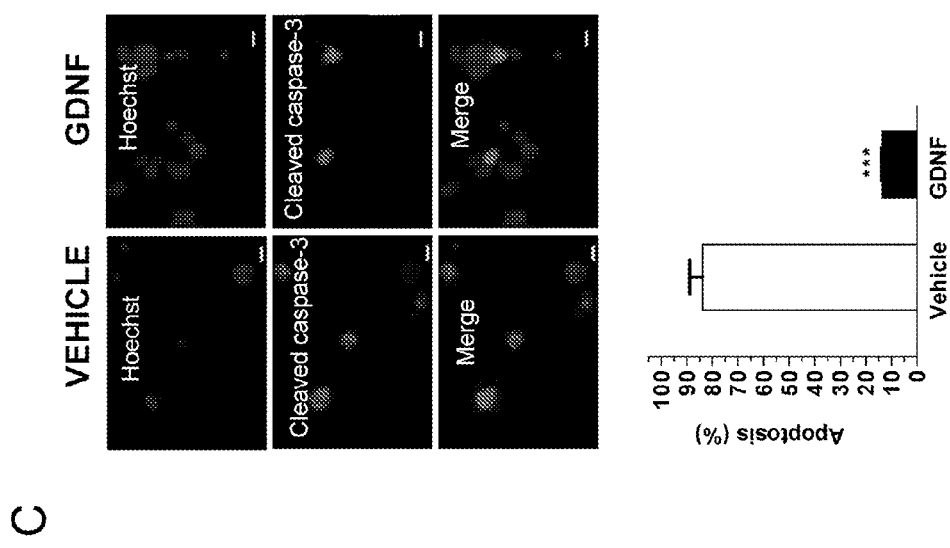

The methods and compositions described herein are based on the discovery that receptors for GDNF (the GFR-α and c-Ret complex) are present on β-cells and that activation of the GDNF receptors promotes β-cell survival, proliferation and protects the β-cells from apoptosis. Furthermore, transgenic mice that overexpressed GDNF in glia exhibit increased β-cell mass, proliferation and insulin content and exhibit resistance to experimentally induced β-cell loss and subsequent hyperglycemia. As β-cell dysfunction or death and resulting hyperglycemia are hallmarks of diabetes, the methods and compositions herein provide treatments of and intervention for diabetes. The methods and compositions taught herein are optionally used in conjunction with additional treatments, such as insulin administration.

Provided herein are compositions that include GDNF receptor agonists. GDNF receptor agonists include GDNF, variants of GDNF, fragments of GDNF, small molecules and the like that activate the GFR-α and c-Ret complex. Such activation of the GFR-α and c-Ret complex, for example, causes phosphorylatin of Akt and GSK3β. Thus, in screening for compounds that are GDNF receptor agonists, one of skill in the art could detect, for example, binding of the agonists and the receptor, phosphorylation or Akt or GSK3β, or ay combination. Small molecule agonists include XIB4035. See, for example, Tokugawa et al. (2003) XIB4035, a novel nonpeptidyl small molecule agonist for GFRα-1. Neurochem. Int. 42, 81-86, which is incorporated herein by reference in its entirety for the small molecules taught therein and methods of making and using them.

GDNF (also known as astrocyte derived trophic factor, glial cell line derived neurotrophic factor, glial derived neurotrophic factor, HFB1-GDNF) includes the polypeptide sequence provided as GenBank Accession No. NP_000505 MKLWDVVAVCLVLLHTASAFPLPAGKRP-PEAPAEDRSLGRRRAPFALSSDSNMPED YPDQFD-DVMDFIQATIKRLKRSPDKQMAVL-PRRERNRQAAAANPENSRGKGRRGQ RGKNRGCVLTAIHLNVTDLGLGYETKEE-LIFRYCSGSCDAAETTYDKILKNLSRNRR LVSD-KVGQACCRPIAFDDDLSFLDDNLVYHIL-RKHSAKRCGCI (SEQ ID NO: 9) and its various isoforms and correlates in various species.

Variants (including homologs, mutants, derivatives, and analogs) of GDNF include polypeptides having an amino acid sequence with at least about 80-100% (including at least about 80, 90, 95, 98, or 99% sequence identity) as compared to GDNF. It is understood that one way to define any known variants, of the disclosed polypeptides and the genes encoding them is through defining the variants in terms of the percent identity to specific known sequences. Those of skill in the art readily understand how to determine the percent identity of two polypeptides or nucleic acids. For example, the identity is calculated after aligning the two sequences so that the identity is at its highest level, is performed by published algorithms (e.g., Smith and Waterman Adv. Appl. Math. 2: 482 (1981); Needleman and Wunsch, J. Mol. Biol. 48: 443 (1970); Pearson and Lipman, Proc. Natl. Acad. Sci. U.S.A. 85: 2444 (1988), or by computerized implementations of these algorithms (e.g., GAP, BESTFIT, FASTA, and TFASTA in the Wisconsin Genetics Software Package, Genetics Computer Group, 575 Science Dr., Madison, Wis.).

Numerous variants of GDNF which retain an GDNF receptor agonist function are taught for example by Eketjall et al., Distinct Structural Elements in GDNF mediate binding to GFRα1 and activation of the GFRα1-c-Ret receptor complex, EMBO J. 18 (21):5901-5910, and by U.S. Pat. No. 6,866,851, which are incorporated by reference in their entireties for teachings regarding amino acid variations, specific binding, and agonistic activity and for specific mutants taught therein. For example, variants of GDNF useful in the composition and methods taught herein retain the hydrophobic residues in fingers 1 and 2 of GDNF. Specific examples of variants include K37A+R39A, K81A+K84A, K81A+K84A, R91A, E58A, D109A, V119A, and V119A. Other variants include polypeptides comprising from one to eight amino acids identical to region F2c of GDNF.

Other amino acid variations are also acceptable. Generally, all sequence variants fall into one or more of three classes: substitutional, insertional or deletional variants. Substitution variants are those in which at least one amino acid residue has been removed and a different amino acid residue inserted in its place. Substitutions include conservative and non-conservative substitutions. A conservative substitution is a substitution of an amino acid residue for another amino acid residue having similar biochemical properties. Typically, conservative substitutions have little to no impact on the biological activity of a resulting polypeptide. Conservative substitutions include those shown in Table 1.

TABLE 1

Conservative Amino Acid

| Original Residue | Substitutions Exemplary Substitutions |
|---|---|
| Arg | Lys |
| Asn | Gln |
| Asp | Glu |
| Cys | Ser |
| Gln | Asn |
| Glu | Asp |
| Gly | Pro |
| His | Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Insertion variants are those in which one or more amino acid residues (e.g., 1-10) are introduced into a predetermined site. Deletion variants are characterized by the removal of one or more amino acid residues (e.g., 1-30). Deletions or insertions preferably are made in adjacent pairs; i.e. a deletion of 2 residues or insertion of 2 residues. Substitutions, deletion, insertions or any combination thereof may be combined to arrive at a final construct. These variants ordinarily are prepared by site specific mutagenesis of nucleotides in the DNA encoding the GDNF agonist, thereby producing DNA encoding the variant, and thereafter expressing the DNA in recombinant cell culture.

While the site for introducing a sequence variation is predetermined, the mutation per se need not be predetermined. For example, in order to optimize the performance of a mutation at a given site, random mutagenesis may be conducted at the target region and the expressed GDNF variants screened for the optimal combination of desired activity. Techniques for making substitution mutations at predetermined sites in DNA having a known sequence are well known.

A polypeptide is produced to contain one or more amino acid variations by manipulating the nucleotide sequence that encodes that polypeptide using, for example, standard procedures such as site-directed mutagenesis. Alternatively, a polypeptide is produced to contain one or more variations by using standard peptide synthesis methods. Polypeptide fragments are optionally produced enzymatically.

It is understood that there are numerous amino acid and peptide analogs (e.g., D amino acids) are optionally incorporated into the disclosed variants. These amino acid analogs are readily incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10): 400-403 (1989); Benner, TIB Tech, 12:158-163 (1994); Ibba and Hennecke, Bio/technology, 12:678-682 (1994) all of which are herein incorporated by reference at least for material related to amino acid analogs).

Variants also include molecules that resemble peptides but lack a natural peptide linkage. For example, linkages for amino acids or amino acid analogs include $CH_2NH$—, —$CH_2S$—, —$CH_2$—$CH_2$—, —CH=CH— (cis and trans), —$COCH_2$—, —$CH(OH)CH_2$—, —$CHH_2SO$—, —$CH_2NH$—, and $CH_2CH_2$— (Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3; Morley, Trends Pharm Sci (1980) pp. 463-468; Hudson, D. et al., Int J Pept Prot Res 14:177-185 (1979); Spatola et al. Life Sci 38:1243-1249 (1986); Hann J. Chem. Soc Perkin Trans. I 307-314 (1982); Almquist et al. J. Med. Chem. 23:1392-1398 (1980); Jennings-White et al. Tetrahedron Lett 23:2533 (1982); Szelke et al., EP 45665 CA (1982); Holladay et al. Tetrahedron. Lett 24:4401-4404 (1983); and Hruby Life Sci 31:189-199 (1982), each of which is incorporated herein by reference in its entirety at least for amino acid linkages and methods of utilizing them.

In one example, a biological activity (e.g., ligand binding or phosphorylation of Akt or GSKβ3) of the GDNF variant is not decreased, as compared to wild-type GDNF, by more than 25%, for example not more than 20%, for example not more than 10% upon amino acid variation.

Provided herein are nucleic acids that encode the GDNF receptor agonists, including GDNF and all variants of GDNF, and receptors and subunits thereof that retaining the desired biological activities. Also provided are vectors and cells including the nucleic acids or their complements.

Provided herein are pharmaceutical compositions comprising the GDNF receptor agonist and a pharmaceutically acceptable carrier. By pharmaceutically acceptable carrier is meant a material that is not biologically or otherwise undesirable, i.e., the material upon administration to a subject causes few or no undesirable biological effects or deleterious interactions with other components of the composition. Suitable carriers and their formulations are described in *Remington: The Science and Practice of Pharmacy*, 21$^{st}$ *Edition*, David B. Troy, ed., Lippicott Williams & Wilkins (2005).

Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained release preparations such as semipermeable matrices of solid hydrophobic polymers containing the GDNF receptor agonist. Matrices are in the form of shaped articles, e.g., films, liposomes or microparticles. One of skill in the art selects the carrier and formulation, for instance, based on the route of administration and concentration of the composition being administered.

Pharmaceutical compositions optionally include carriers, thickeners, diluents, buffers, preservatives, surface active agents, and the like. Pharmaceutical compositions may also include one or more active ingredients such as antimicrobial agents, anesthetics, or agents used to treat diabetes.

A transplant composition is provided which includes one or more GDNF-receptor-agonist secreting cells (e.g., glial cells) and one or more insulin secreting cells. (e.g., β-cells). Optionally, the composition also includes exogenous GDNF (e.g., in a defined medium). The concentration of GDNF is as described below. The transplant composition, like pharmaceutical compositions, optionally include various additional factors. Such factors include enzymes, antimicrobials, and the like.

Optionally, the GDNF-receptor-agonist secreting cells, such as glial cells, in the transplant composition are genetically modified to express or overexpress GDNF or GDNF receptor agonist. As another option, which is used separately or in combination with other options disclosed herein, the insulin secreting cells are genetically modified to express or over express GFR-α1 and c-Ret.

Cells are genetically modified using techniques within the artisan's skill, which are described below. Nucleic acids that encode GFR-α1, c-Ret, GDNF receptor agonists, or variants are provided in the art. Expression is assayed utilizing standard techniques. Initial screening, for example, is accomplished by Southern blot analysis or PCR techniques to analyze whether integration of the transgene has taken place. The level of expression is assessed using techniques which include, but are not limited to, Northern blot analysis or PCR.

Insulin secreting cells (e.g., β-cells) and GDNF-receptor-agonist secreting cells (e.g., glial cells) are derived from any number of sources. The cells are derived, for example, from living donors or cadaveric donors. The donor is the same species as the recipient (e.g., allogeneic) or a different species than the recipient (e.g., xenogeneic). In some cases the donor and the recipient are the same individual (e.g., autologous). Insulin secreting cells optionally are surgically removed from the pancreas of the donor. GDNF-receptor-agonist secreting cells are optionally derived from enteric or neural tissue surgically removed from a donor. The cells, however, are optionally derived from cells lines or genetically modified cells or tissues.

In one aspect, provided herein are in vitro methods. Such methods are useful, for example, to enhance the number and health of insulin secreting cells in a culture, including for example, in a culture of cells to be transplanted into a transplant recipient. Insulin secreting cells include β cells isolated from pancreatic islets but could also include insulin secreting cells from a cell line or from stem cells expanded and/or differentiated in culture. Furthermore, insulin secreting cells also include cells genetically modified to express insulin or to over express insulin.

Thus, provided herein is a method of enhancing a population of insulin secreting cells (e.g., pancreatic islet cells) for transplantation. The method includes culturing the cell population with an exogenous GDNF receptor agonist (for example, GDNF). The agonist is optionally provided in a defined culture medium (i.e., a medium that excludes serum). The concentration of GDNF in the culture is at a concentration of about 1-2000 ng/ml, including at least about 10 ng/ml, at least about 100 ng/ml, and at least about 200 ng/ml. This method enhances the insulin secreting cells in at least one or more ways, including, for example, by increasing the number of viable cells (e.g., by increasing proliferation) as compared to a control or by reducing apoptosis as compared to a control. Since the total number of insulin secreting cells is increased by promoting proliferation or by reducing cell death, there are more cells to release insulin. Thus the population of insulin secreting cells is enhanced to release more insulin as compared to a control.

Also provided herein is a method of preparing an insulin secreting cell population (e.g., a pancreatic islet cell population) for transplantation from a living donor. Although cadaveric donors are most commonly used today, live donors of the same or different species have also been utilized. The utilization of live donors is optimized if more insulin producing cells are obtained. Thus the present method includes administering a GDNF receptor agonist to a transplant donor and isolating an insulin secreting cell population (e,g, a pancreatic islet cell population) from the donor. The method optionally further includes culturing the isolated cell population with GDNF or other GDNF receptor agonist and/or culturing the isolated cell population with a cell, such as a glial cell that produces GDNF or other GDNF receptor agonist.

Methods of treating diabetes (type 1 or type 2) are also provided herein. For example, provided herein is a method of treating type-1 diabetes in a subject. The method includes the steps of selecting a subject with type-1 diabetes and administering to the subject a GDNF receptor agonist. Similar methods are useful to prevent type 1 diabetes in a subject at risk for developing type 1 diabetes. Thus a method of a method of preventing type-1 diabetes in a subject includes selecting a subject at risk for type-1 diabetes and administering to the subject a GDNF receptor agonist.

One of skill in the art identifies and selects subjects with type 1 diabetes and subjects at risk for developing type 1 diabetes using any methods of diagnosis and identification. For example, diagnosis is based on an elevated blood glucose level after fasting or on a glucose tolerance test. Furthermore, diagnosis of type 1 diabetes includes various physical symptoms and characteristics. Type 1 diabetes usually begins before age 40. In the United States, the peak age at diagnosis is around 14 years of age and the earliest symptoms (including, e.g., weight loss) are associated with hyperglycemia.

Identification of a subject at risk for developing type 1 diabetes is also within an artisan's skills. For example, a subject at risk for type 1 diabetes is an individual with a genetic predisposition or an individual with a surgically excised pancreas or portion thereof. A subject with a surgically removed pancreas includes a subject with chronic pancreatitis or a subject with an injury necessitating surgical removal of the pancreas.

Subjects with insulin dependent type 2 diabetes or at risk for developing type 2 diabetes similarly benefit from the administration of a GDNF receptor agonist. Thus, provided herein is a method that includes the steps of selecting a subject with, or at risk of developing, type-2 diabetes and administering to the subject a GDNF receptor agonist. Diagnosis is usually based on fasting glucose levels, on a glucose tolerance test, or on the level of blood insulin. Type 2 diabetes, unlike diabetes type 1, usually develops in middle age or later and is frequently associated with obesity. Insulin levels in subjects with type 2 diabetes are usually normal or higher than average, although glucose levels are generally elevated.

The compositions herein are administered in a number of ways. Transplant compositions are frequently administered intrahepatically, for example. In some cases, several transplants are necessary. One of skill in the art, however, readily determines the concentration of cells to include in the transplant composition and recognizes the need for a second or subsequent transplant based on such clinical signs as hyperglycemia and the like. Administration of pharmaceutical compositions may be topical, by inhalation, parenteral (for example, intravenous), subcutaneous, intraperitoneal or intramuscular. Sustained release or slow release systems such that a constant dosage is maintained are useful in the methods taught herein. For additional discussion of suitable formulations and various routes of administration of therapeutic compounds, see, e.g., Remington: The Science and Practice of Pharmacy (21st ed.) eds. A. R. Gennaro et al., University of the Sciences in Philadelphia 2005.

Effective dosages and schedules for administering the compositions is determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage varies with the age, condition, sex and extent of the disease in the patient, route of administration, or whether other drugs are included in the regimen, and are determined by one of skill in the art. The dosage is adjusted by the individual physician in the event of any contraindications. A typical dosage of the provided compositions used alone ranges in a human subject, for example, from about 1 µg up to about 1000 µg of GDNF administered at least once, with variations depending on the factors mentioned above. For example, a dosage of about 10-100 µg of GDNF administered subcutaneously 2 to 3 times a week is used in a typical human. As one variation, a slow release form of GDNF or other GDNF receptor agonist is implanted into the pancreas or liver. With a local slow release form, the dosage is, for example, 1-10 ng (including, e.g., 5 ng) of GDNF or other agonist of comparable stability and binding affinity.

Administration of a GDNF receptor agonist optionally is combined with administration of insulin and/or with administration of sulfonylureas, meglitinides, biguanides (e.g., metformin), thiazolidinediones, DPP-4 inhibitors, and/or α-glucosidase inhibitors. It is within the artisan's skill to adjust the dosage levels appropriately for such combination therapy. Coadministration reduces the dosage for any one of the agents. Such reductions are generally determined by monitoring blood glucose levels.

The methods taught herein for preparing a population of islet cells for transplantation are also combined with treatment. Thus, for example, provided herein is a method of treating diabetes in a subject that includes the steps of preparing an insulin secreting cell population (e.g., an pancreatic islet cell population) for transplantation according to any one of the in vitro method described above and transplanting the cell population to the subject to be treated (i.e., to the transplant recipient). The transplant recipient is optionally also administered a GDNF receptor agonist before, after or during the transplantation.

Also provided herein is a method of treating diabetes (type 1 or type 2) in a subject by administering to the subject a transplant composition comprising glial cells and insulin secreting cells or by administering to the subject a transplant composition comprising insulin secreting cells (e.g., β cells) genetically modified to over express GFR-α1 and c-Ret.

It is within the skill of one in the art to genetically modify an insulin secreting cell to over express GFR-α1 and c-Ret. Sequences for the amino acids and the nucleic acids that encode them are known in the art. Thus, one or more nucleic acids that encode GFR-α1, c-Ret, or both are introduced into a target cell (e.g., an insulin secreting cell) using any one of several methods, including, for example, physical methods (e.g., electroporation, direct gene transfer and particle bombardment), chemical methods (e.g. lipid-based carriers and other non-viral vectors), and biological methods (e.g. virus derived vectors).

With any of the methods of treatment that include a transplantation step, the transplant recipient is optionally administered a GDNF receptor agonist (e.g., GDNF) before, after or during the transplantation procedure.

As used herein, subject includes, but is not limited to, a vertebrate, more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, as well as fetuses, whether male or female, are intended to be covered. The term subject includes human and veterinary subjects.

Inhibit, inhibiting and inhibition mean to decrease expression, an activity, response, condition, disease, or other biological parameter. This includes, but is not limited to, the complete ablation of the expression, activity, response, condition, or disease. This may also include, for example, a 10% reduction in expression, activity, response, condition, or disease as compared to the native or control level. Thus, the reduction is 10, 20, 30, 40, 50, 60, 70, 80, 90, 100%, or any amount of reduction in between as compared to native or control levels.

As used throughout, controls are generally cells, cultures, or subjects which are untreated with the GDNF receptor agonist but also include treated cells before or after the effect of the GDNF receptor agonist.

By exogeneous is meant that the agent or condition is specifically provided non-naturally. When an agent is exogenously provided to a cell culture, for example, the agent may or may not already be present based on natural secretion by the cells, but in either case, additional agent is added from an external source. Such an external source is optionally not serum but is instead a component of a defined medium.

As used herein the terms protein, polypeptide and peptide are used interchangeably and are not meant to designate a specific number of amino acid residues.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

Publications cited herein and the material for which they are cited are hereby specifically incorporated by reference in their entireties. No admission is made that any reference constitutes prior art. The discussion of references states what their authors assert, and applicants reserve the right to challenge the accuracy and pertinence of the cited documents.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure.

EXAMPLES

Example 1

Ret and GFRα1 Receptors are Expressed in β-TC-6 Cells and Mouse Pancreatic β-Cells Antibodies.

The following antibodies were used for immunocytochemistry I nthis and subsequent Examples: rabbit polyclonal antibodies to GDNF (D-20) and GFRα1 (H-70) (Santa Cruz Biotechnology, Santa Cruz, Calif.), human c-Ret (R787: IBL, Japan), Ki67 (Novocastra, Newcastle, U.K.), S-100β (BD Pharmingen, San Diego, Calif.), cleaved caspase-3 (Cell Signaling Technologies, Beverly, Mass.), and guinea pig anti-insulin (Zymed Laboratories, San Francisco, Calif., U.S.A.) were used at 1:50 dilution. Biotin-conjugated donkey anti-rabbit IgG secondary antibody and peroxidase-conjugated streptavidin (Jackson ImmunoResearch Laboratories, Westgrove, Pa.), Alexa Fluor 488 and 594 donkey anti-guinea pig and rabbit IgG (Molecular Probes, Eugene, Oreg.) were used at a 1:500 dilution.

For Western blotting, rabbit polyclonal antibodies to phospho-Akt (ser473), Akt, and phospho-GSK3β, GSK3β and cleaved caspase 3 (Cell Signaling Technologies) were used at a 1:1000 dilution, streptavidin-horseradish peroxidase conjugated anti-rabbit and anti mouse IgG (Cell Signaling Technologies) at 1:2500 dilution, and mouse monoclonal antibody to β-actin (Sigma, St. Louis, Mo., U.S.A.) at 1:5000 dilution.

Islet Isolation and Cell Culture.

Islets were isolated using a modification of the procedure described by Bernal-Mizrachi et al. (J Clin Invest 2001; 108: 1631-8). Pancreata were digested for 40 min at 37° C. with 2 mg/ml collagenase (Type IV, Gibco BRL, Grand Island, N.Y., U.S.A.), and islets isolated by density gradient centrifugation using 1.108, 1.096, and 1.037 islet gradient (Mediatech Inc., Herndon, Va.). To obtain single cells, islets were digested with 0.01% trypsin in modified Eagle's medium and dispersed by gently pipetting up and down. β-TC-6 cells (ATTC, Manassas, Va.) were cultured in Dulbecco's Modified Eagles' Medium (DMEM) (ATCC) supplemented with 15% fetal bovine serum. For GDNF stimulation studies cells were serum deprived for 48 hours, followed by incubation with DMEM alone or DMEM supplemented with different concentrations of GDNF.

PCR.

First-strand cDNA synthesized using the Omniscript reverse transcription kit (Qiagen GmbH, Hilden, Germany) from RNA isolated using the RNeasy Mini kit (Qiagen) was subjected to 40 cycles of PCR amplification. The primers used included mouse GFRα1 forward (5'<ATGAAGAAC-GAGAGAGGCCCAA>3') (SEQ ID NO:3) and reverse (5'<ACTCTGGCTGGCAGTTGGTAAA>3') (SEQ ID NO:4) primers, Ret forward (5'<TACCGTACACGGCTG-CATGAGAAT>3') (SEQ ID NO:5) and reverse (5'<6>3') (SEQ ID NO:6) primers, and GDNF forward (5'<TCGATAT-TGCAGCGGTTCCTGT>3') (SEQ ID NO:7) and reverse (5'<ACATCCACACCGTTTAGCGGAA>3') (SEQ ID NO:8) primers. The primers used to quantify GDNF were designed to span at least an intron and thus are able to discriminate between products amplified from mRNA and genomic DNA.

Immunocytochemistry.

In all Examples herein, β-TC-6 cells, isolated pancreatic β-cells, and pancreatic sections from frozen and paraffin-embedded tissues were stained for immunofluorescence microscopy as previously described (Mwangi et al. Neuroscience 2006; 143:241-51) and analyzed on a Zeiss Axioskop 2 plus fluorescent microscope mounted with an AxioCam MRc 5 camera (Carl Zeiss Werk, Gottingen, Germany). Images were taken with the aid of the Axiovision (Rel 4.5) software (Carl Zeiss Imaging System). Cells were also scanned with an LSM 510 laser scanning confocal microscope (Zeiss, Heidelberg, Germany).

Results. To understand the role of GDNF in β-cell growth and survival, the expression of its receptors in cells of the insulin-secreting mouse pancreatic β-TC-6 cell line and mouse pancreatic β-cells were analyzed by RT-PCR. As seen in FIG. 1A, both cell types express significant amounts of GFRα1 and Ret receptor mRNA. The expression of the receptors was further analyzed by immunofluorescence microscopy using receptor-specific antibodies. High expression of both receptors was observed in cultured β-TC-6 cells and isolated mouse pancreatic β-cells (FIGS. 1B and C). The localization of the receptors on the surface of the cells was confirmed by laser confocal microscopy (FIG. 1D).

Example 2

GDNF Promotes β-Cell Survival and Proliferation In Vitro by Activating the PI-3-K/Akt Signaling Pathway Apoptosis.

Apoptosis was assessed either by Western blotting for cleaved caspase-3 or cleaved caspase-3 with immunofluorescence microscopy (Mwangi et al. Neuroscience 2006; 143: 241-51).

Proliferation.

Cell proliferation in cultured cells and pancreatic tissue was assessed by immunofluorescence microscopy (Anitha et al. Gastroenterology 2006; 131:1164-78) using an anti-Ki67 polyclonal antibody (Teta et al. Diabetes 2005; 54:2557-67).

Western Blotting.

Western blotting were performed in all Examples as previously described (Mwangi et al. Neuroscience 2006; 143: 241-51). A semiquantitative measurement of band density was performed using Scion Image for Windows software (Scion Corp, MD).

Statistical Analysis.

All statistical analyses in this and other Examples were conducted using the GraphPad Prism software version 3.00 for Windows (GraphPad Software, San Diego Calif.). Data were tested for normality and subjected to t-tests or One-way ANOVA with Tukey post test.

Results.

GDNF is known to be a trophic factor for neurons, but its role in β-cell growth and survival was previously unknown. GDNF (10-500 ng/ml) is shown here, however, to play a role in preventing apoptosis and in promoting proliferation of primary β-cells and β-TC-6 cells. Apoptosis was assessed by blotting for cleaved caspase-3 and cleaved caspase-3 immunocytochemistry. GDNF treatment for 72 h suppressed cleaved caspase 3 expression in β-TC-6 cells in a dose-dependent fashion (FIGS. 2A and B). To further investigate the ability of GDNF to promote β-cell survival, the ability of GDNF to block the effects of thapsigargin, a pro-apoptotic stimulus for β-cells, was assessed. Exposure of β-TC-6 cells to 0.1-μM thapsigargin for 24 h resulted in a significant reduction in apoptosis in the presence of GDNF (FIG. 2C). Similarly isolated mouse pancreatic β-cells from the MIP-GFP mice revealed a significant reduction in apoptosis in cells cultured for 48 h in the presence of GDNF (100-500 ng/ml) compared to vehicle (FIG. 2D). Immunohistochemistry was performed as described in Example 1.

The effect of GDNF in promoting the proliferation of β-cells in vitro was also assessed. β-TC-6 cells deprived of serum for 48 h were cultured in the presence or absence of GDNF for 24 h and assessed for proliferation by staining for the proliferation marker Ki6717. GDNF increased the number of Ki67 positive cells in a dose dependent fashion (FIG. 2E). Taken together these data show an important survival and proliferation role for GDNF in β-cells in vitro.

Figures 2, 3:
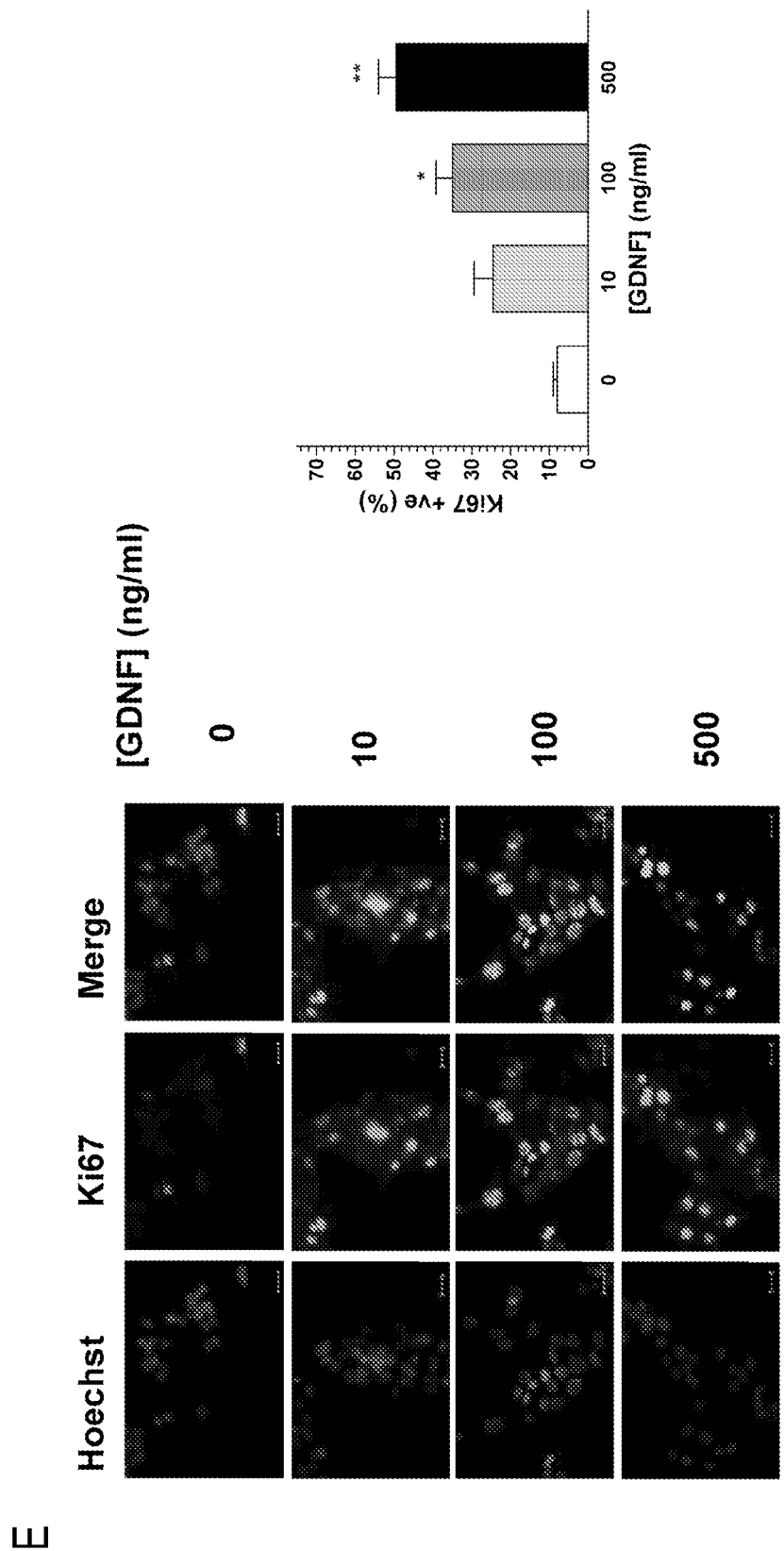
FIG. 3 shows Western blots and histograms indicating GDNF stimulates Akt phosphorylation and its downstream target GSK3β in β-TC-6 cells.

Since GDNF signals through the PI-3-kinase/Akt pathway in neurons to promote cell survival, the possible activation of this pathway in β-cells by GDNF was assessed. β-TC-6 cells deprived of serum for 48 h were stimulated with vehicle only (no GDNF), GDNF (100 ng/ml) or serum (15%) for 30 min, and analyzed by Western blotting for phospho-Akt (ser 473). Significant amounts of phospho-Akt were detected in cells cultured in the presence of GDNF, while none were detected in cells cultured in vehicle only (P<0.001; FIG. 3A). The ability of GDNF to stimulate the phosphorylation of glycogen synthase kinase-3β (GSK3β), a downstream target of Akt, was also assessed in these cells. More than 2.7 fold more phospho-GSK3β (ser9) was detected by Western blotting in β-TC-6 cells cultured for 30 min with GDNF than in cells cultured in vehicle only (P<0.001; FIG. 3B). This increase was lost when the cells were cultured with GDNF in the presence of the PI3-kinase inhibitor LY294002. These data, thus, demonstrate that GDNF activates the PI-3-K/Akt signaling pathway in β-cells in vitro.

Example 3

Mice Over Expressing GDNF in Pancreatic Glia have Higher β-Cell Mass and β-Cell Proliferation Animals.

In vivo studies were conducted in littermates obtained from crossing CF1 WT mice with GFAP-GDNF transgenic mice on a CF1 background generated at Washington University, St. Louis, Mo. GFAP-GDNF transgenic mice were engineered to overexpress GDNF in glial cells under the control of the glial fibrillary acidic protein promoter 10. The genotypes of the mice were determined by PCR using DNA extracted from mouse tail using the REDExtract-N-Amp Tissue PCR Kit (Sigma-Aldrich CO, St. Louis, Mo.) according to the manufacturer's recommended procedure, using as primers the forward (5'-AGACGCATCACCTCCGCT-3') (SEQ ID NO:1) and reverse (5'-TGACGTCATCAAACTGGTCAGG-3') (SEQ ID NO:2) primers, which were designed to only amplify the transgene sequence.

MIP-GFP transgenic mice (Hara et al. Transgenic mice with green fluorescent protein-labeled pancreatic beta-cells. Am J Physiol Endocrinol Metab 2003; 284:E177-83) were used for in vitro studies to isolate primary beta cells. These mice express green fluorescent protein (GFP) in pancreatic β-cells under the control of the mouse insulin I promoter (MIP). Mice were used at 8-10 weeks of age.

Immunohistochemistry.

Pancreata were frozen in Tissue-Tek 0. C. T. compound (Sakura Finetek, Torrance, Calif.) or fixed in 10% formalin solution and embedded in paraffin using standard techniques. Sections were fixed or deparaffinized and rehydrated according to suggested protocols (Cell Signaling Technologies). Staining was performed according to standard protocols using the Histomouse-SP (AEC broad spectrum) kit (Zymed, South San Francisco, Calif.).

Assessment of β-Cell Mass and Size.

Four 5 μm pancreas sections (separated by 200 μm)/per mouse were used to assess β-cell mass as previously described 3. Images were taken after insulin staining, and islet size, islet number, β-cell size and the total areas of the sections determined using the Image-Pro Plus 5.0 software (Media Cybernetics, Silver Spring, Md.). The percentage of β-cell area in each pancreas was then determined.

Assessment of Insulin Content.

Pancreata were homogenized using acid alcohol as previously described (Montana et al. Beta cell mass and growth after syngeneic islet cell transplantation in normal and streptozocin diabetic C57BL/6 mice. J Clin Invest 1993; 91:780-7), and insulin levels measured by radioimmunoassay at Linco Diagnostic Services (St. Louis, Mo.).

Results.

In view of the effects of GDNF in vitro, the effects of GDNF in vivo was next assessed using a GDNF transgenic (GDNF-tg) mouse in which over expression has been demonstrated in astrocytes in the brain and spinal cord (Zhao et al. Exp Neurol 2004; 190:356-72) and in the glia in the peripheral nervous system. Experiments were performed on GDNF-tg mice and their WT littermates. Both male and female GDNF-tg mice have 20% lower body weight compared to their WT littermates (weight in gms at 8 weeks, WT-M: 35.1+1.4, GDNF-tg M: 30.8+0.7 P<0.05, WT-F: 29.5+0.8, GDNF Tg F: 23.7+1.2, P<0.01). Despite this weight loss, the GDNF-tg mice have normal eye opening, fur growth, weaning and reproduction capacity, similar to WT mice. GDNF-tg mice have a slight tremor at birth that disappears by 2-3 weeks of age. To confirm the over expression of GDNF in the pancreas of GDNF-tg mice, the levels of GDNF mRNA in pancreas from WT and GDNF-tg mice were compared by RT-PCR as described above. GDNF-tg mice had more than 2.2 fold more GDNF message than WT mice (P<0.01; FIG. 4A). To identify the specific areas of the pancreas where GDNF is expressed, sections of pancreas from both WT and GDNF-tg mice were analysed by immunofluorescent microscopy (FIG. 4B). As seen in the images, the GDNF expression was localized to glial cells identified by the glial specific marker, S-100β. GDNF expression was enhanced in the GDNF-tg mice compared to WT mice.

Figures 2, 5:
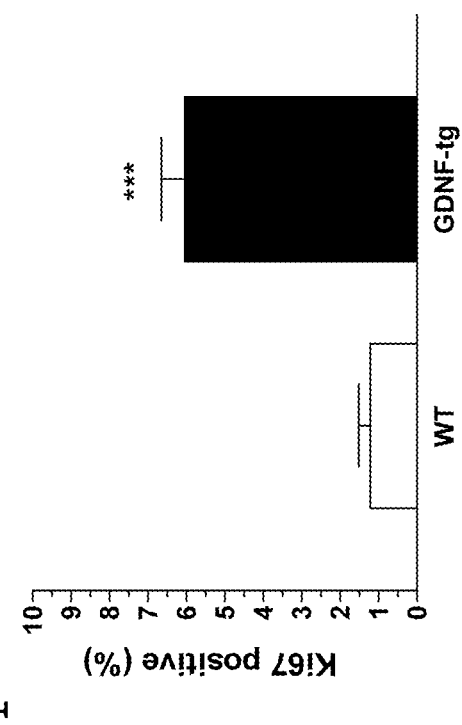
FIG. 5 shows that GDNF transgenic mice have higher β-cell mass and increased proliferation compared to WT mice.

To assess the effects of increased GDNF expression in the pancreas, successive sections taken 200 μm apart from pancreata from 8 week-old WT and GDNF-tg mice were stained for insulin. Examination of these sections revealed significantly more islets in GDNF-tg mice than their WT littermates (FIG. 5A). A more detailed morphometric analysis to assess β-cell mass showed a 2.5 fold increase in β-cell area/pancreas in transgenic mice compared to WT mice (P<0.001; FIG. 5A). The number of islets per unit pancreatic tissue was higher in GDNF-tg mice compared to WT mice (P<0.05; FIG. 5B). The size of individual islets was higher in GDNF-tg mice compared to WT mice (P<0.05; FIG. 5C). However, individual β-cell size appeared similar (P>0.05; n=26, FIG. 5D) and no change in the islet architecture was noted, with a similar distribution of β and α cells. Assessment of pancreatic insulin content also revealed a 3.2 fold higher insulin content in GDNF-tg mice than in WT mice (P<0.05; FIG. 5E). To understand the processes accounting for the increased beta cell mass in GDNF-tg mice, WT and GDNF-tg mice were stained for insulin and Ki67 to assess β-cell proliferation (FIG. 5F). A significantly higher number of ki67+/insulin+ cells were observed in islets of GDNF transgenic mice compared to WT mice. (P<0.0001, n=3).

Example 4

Improved Glucose Homeostasis in GDNF Transgenic Mice

Glucose Tolerance Test and Estimation of Insulin Sensitivity.

Age-matched WT and GDNF-tg mice were fasted for 6 h and baseline blood glucose levels measured with the aid of an Accu-Check Advantage blood glucose meter (Roche, Mannheim, Germany) using blood collected from the tail vein. To test for glucose tolerance, the mice were injected intraperitoneally with 2 mg glucose/g body weight in sterile PBS and blood glucose levels measured 30, 60 and 120 min after injection (Bernal-Mizrachi et al. Islet beta cell expression of constitutively active Akt1/PKB alpha induces striking hypertrophy, hyperplasia, and hyperinsulinemia. J Clin Invest 2001; 108:1631-8). For the insulin sensitivity test, fasted mice were injected intraperitoneally with 0.75 U/Kg human rapid insulin (Eli Lilly Co, Indianapolis, Ind.), blood glucose measured 15, 30, 60, 90, and 120 min after injection (Lauro et al. Nat Genet 1998; 20:294-8).

Assessment of Insulin and c-Peptide Secretion.

To analyze insulin secretion in vivo, blood was collected from 6 h-fasted mice and plasma c-peptide and insulin analyzed by radioimmunoassay (Linco). For in vivo insulin secretion, 6-h-fasted mice were injected with 3 mg/Kg glucose and plasma insulin measured 0 and 2.5 min post-injection using a Rat/mouse insulin ELISA kit (Linco). For in vitro insulin secretion analysis, isolated islets were cultured overnight in Ham's F 10 medium. Forty (40) islets were cultured per well for 2 h in Kreb's Ringer bicarbonate buffer containing 1.67 mM glucose followed by 1 h in buffer containing 1.67 mM or 20 mM glucose. The culture media were collected, the islets lysed in acid-alcohol and insulin concentrations measured by insulin ELISA (Linco).

Results.

To assess the functional effect of increased β-cell mass on glucose homeostasis, glucose tolerance tests were conducted in male and female WT and GDNF-tg mice. Fasting blood glucose levels of GDNF-tg mice of both sexes were significantly (P<0.05) lower than those of WT mice (FIG. 6A, B). Following intraperitoneal glucose administration, blood glucose levels remained significantly lower in GDNF-tg mice than in WT mice at all time points except at the 120 min time point in females (FIG. 6A, B). No difference in insulin sensitivity between WT and GDNF-tg mice using an intraperitoneal insulin sensitivity test was found (FIG. 6C). To investigate the factors contributing to the improved glucose tolerance, c-peptide and insulin levels were assessed in plasma samples collected following 6 hr of fasting. GDNF-tg mice had similar plasma c-peptide and insulin levels to WT mice (P>0.05; FIG. 6 D, E). The glucose-stimulated insulin release assessed at 2.5 minutes after intraperitoneal glucose administration was significantly higher in the GDNF-tg mice compared to WT mice (FIG. 6F, p<0.01). These data support the findings of an increased insulin release in response to a glucose load in the GDNF-tg mice compared to WT mice and explain the improved glucose tolerance. The data also show that the increased β-cell mass seen in GDNF-tg mice resulted in lower fasting blood glucose levels and improved glucose tolerance. The effect of GDNF on insulin secretion in isolated islet was also determined by evaluating glucose-stimulated (20 mM) insulin secretion from isolated islets. Glucose-stimulated insulin secretion in was (% insulin release WT:Tg, n=4).

Example 5

GDNF Transgenic Animals are Resistant to the Induction of Diabetes Mellitus

Resistance to Induction of Diabetes.

WT and GDNF-tg littermates were injected intraperitoneally with 75 mg/Kg streptozotocin followed by another 75 mg/kg streptozotocin after 12 h and their blood glucose levels were measured once daily to monitor onset of hyperglycemia. Hyperglycemia was defined as post-prandial blood glucose greater than 145 mg/dL. At the end of the experiments, the mice were sacrificed, pancreata embedded in paraffin, sectioned and stained for insulin and islet images obtained. The outlines of islets were marked and the images thresholded based on insulin staining intensity and threshold area relative to total islet area calculated with the aid of the MetaMorph Offline version 7.0r3 software (Molecular Devices Corp., Downingtown, Pa.).

To assess apoptosis, pancreas sections from STZ-treated mice were made and apoptosis assessed by cleaved caspase-3 immunofluorescence microscopy with TUNEL staining (Mwangi et al. Neuroscience 2006; 143:241-51).

Results.

Figures 1, 7:
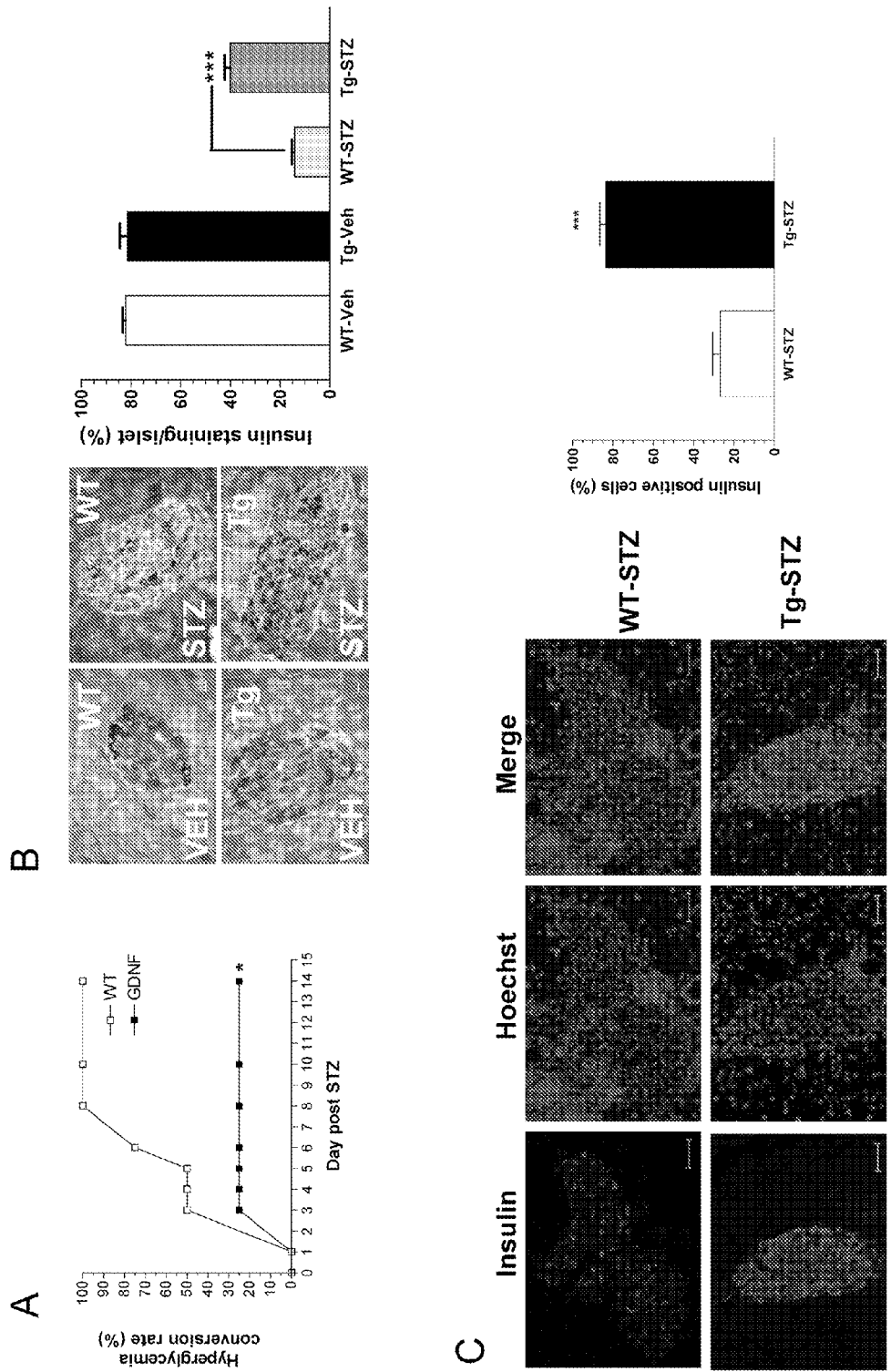
FIG. 7 shows that GDNF transgenic mice are more resistant to STZ-induced diabetes than WT mice using a graph of diabetes conversion rates in WT and GDNF-tg mice after two injections of streptozotocin (75 mg/Kg) (FIG. 7A); a representative photomicrograph of residual insulin staining in pancreatic islets in pancreas sections from GDNF-tg and WT mice 6 days after STZ or vehicle injection and plot of islet residual insulin staining (expressed as percentage of total islet area for each group, mean+SE, *** P<0.001) (FIG. 7B) (Scale bar, 20 μm); representative sections of STZ injected WT and GDNF-tg pancreas stained for insulin and Hoechst 14 days after injection of STZ and a histogram of average insulin positive cells in WT and GDNF-tg mice (FIG. 7C); a histogram (FIG. 7D, left panel) and representative images showing both cleaved caspase-3 and TUNEL positive cells within islets in pancreas sections from STZ-treated WT and GDNF-tg mice (FIG. 7D, right panel) (Arrows show cleaved caspase-3 and TUNEL positive cells. Arrowheads point at islets. Scale bar, 20 μM.) Assessment of proliferation in STZ-treated WT and GDNF-tg mice; and a histogram (FIG. 7E, left panel) showing the average ki67+ cells in islets of pancreatic sections from STZ-treated WT and GDNF-tg mice labeled for both ki67 and insulin.
Figure 7:
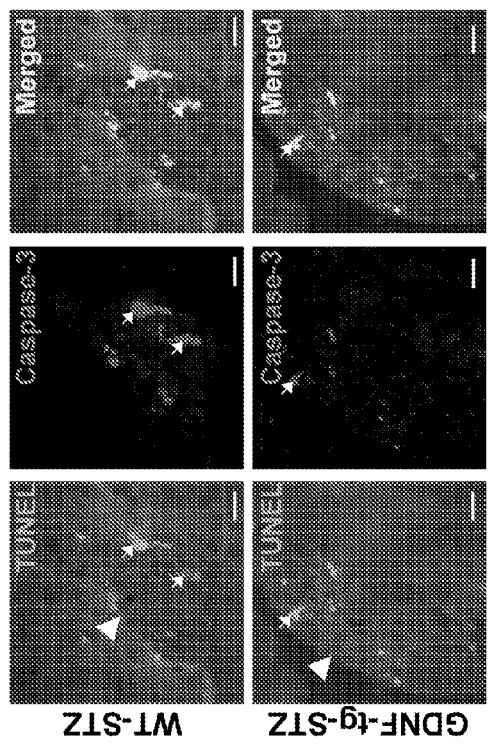
Figure 2:
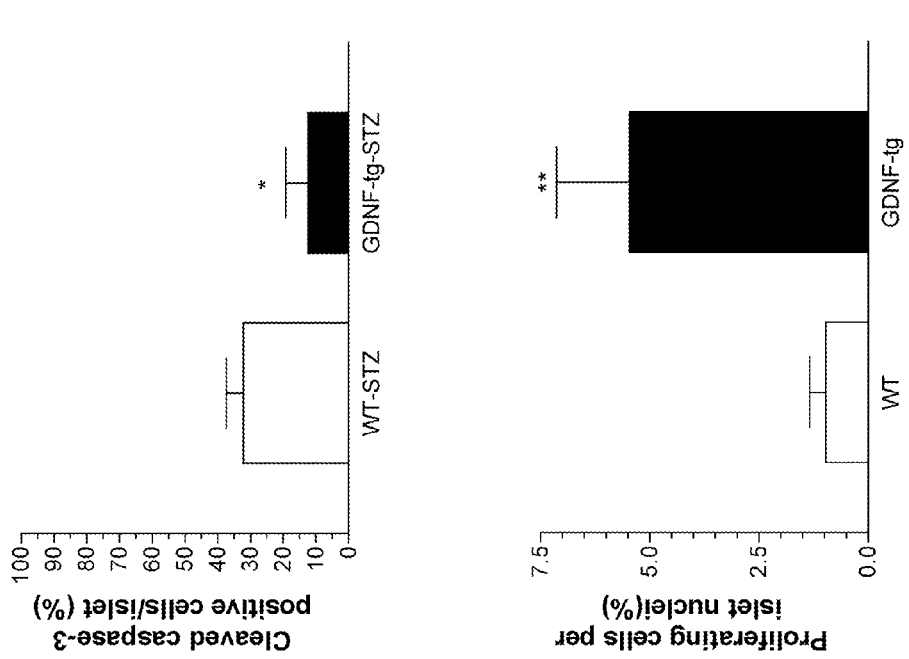

Administration of multiple low doses of streptozotocin (STZ) produces diabetes by the selective loss of β-cells (O'Brien et al. J Pathol 1996; 178:176-81). The rate of conversion to hyperglycemia following a low dose STZ protocol was used to assess diabetes susceptibility. While WT mice developed diabetes as early as day 4 post STZ injection, the GDNF-tg mice remained normoglycemic. At day 14 post STZ injection, the number of hyperglycemic mice was significantly higher among WT mice than GDNF-tg mice (FIG. 7A). The effect of STZ on β-cell mass was assessed by insulin staining as described above. STZ-treatment resulted in over 2.8 fold (P<0.001) reduction in insulin staining in WT mice than in GDNF-tg mice, which would suggest a resistance to STZ-induced destruction of β-cells in the GDNF-tg mice (FIG. 7B, C). Intraperitoneal glucose tolerance curves were compared in weight matched WT and GDNF-tg mice and the impairment in glucose tolerance persisted (blood glucose 30 min post injection of glucose (mg/dl) WT: 252+34, GDNF-tg 175+12, P<0.01, WT weight (gms): 33.73+0.9, GDNF-tg weight (gms): 32.94+0.36, n=5 p>0.05. To determine the mechanisms involved in insulin loss following STZ administration, β-cells apoptosis was assessed by a combination of TUNEL staining (Srinivasan et al. Diabetes 2000; 49:1932-8) with cleaved caspase-3 immunocytochemistry. GDNF-tg mice showed 4 fold less β-cell apoptosis than WT mice twelve days after injection with STZ as evidenced by the smaller number of TUNEL and cleaved caspase-3 positive β-cells in these mice (P<0.05; FIG. 7D). The GDNF-tg mice had enhanced proliferation compared to WT mice (FIG. 7E). As the weight of the mice can affect the amount of STZ administered the WT and GDNF-tg mice were weight matched. The effect of STZ on induction of hyperglycemia was independent of weight as a difference was detected in STZ-induced hyperglycemia in weight matched WT compared to GDNF-tg mice. (Blood glucose (mg/dl) 48 h post STZ, WT: 404+20.16, GDNF-tg: 281+45, P<0.05; weight (gms): WT: 38.3+0.5, GDNF-tg: 39.3+2.1, n=4 p>0.05.)

Example 6

GDNF Treated β-Cells Demonstrate Improved Survival Post Transplantation

To assess the effect of GDNF on transplanted β-cells, the survival of isolated mouse pancreatic islets following hepatic portal vein infusion was assessed. Isolated islets were treated with vehicle or GDNF (100 ng/ml) for 48 h and 200 islets transplanted by hepatic portal vein infusion into each mouse as previously described (Hara et al. A mouse model for studying intrahepatic islet transplantation. Transplantation 2004; 78:615-8). Mice were sacrificed 24 h after transplantation and their livers assessed for the presence of islets by insulin staining, as described above. The number of islets per unit liver tissue area was significantly higher in the GDNF pretreated islet group compared to the vehicle treated islets (number of islets per $cm^2$: GDNF treated, 1.8+0.6; vehicle treated 0.5+0.2, $P<0.05$, n=8). Thus islets treated with GDNF showed improved survival compared to those treated with vehicle alone (FIG. 8). Treatment with GDNF or molecules acting like GDNF-agonists, thus, provides a means to improve post-transplantation β-cell survival.

---

The invention claimed is:

1. A method of enhancing a population of pancreatic islet cells for transplantation comprising culturing the population of pancreatic islet cells with an effective amount of a GDNF polypeptide having SEQ ID NO: 9 or variants with at least 80% sequence identity to SEQ ID NO: 9.

2. The method of claim 1, wherein the GDNF in the culture is at a concentration of at least about 10 ng/ml.

3. The method of claim 1, wherein the GDNF concentration in the culture is at least about 100 ng/ml.

4. The method of claim 1, wherein the GDNF concentration in the culture is at least about 200 ng/ml.

5. The method of claim 1, wherein the pancreatic islet cells in the population are enhanced by increasing the number of viable islet cells as compared to a control.

6. The method of claim 1, wherein the pancreatic islet cells in the population are enhanced by reducing apoptosis as compared to a control.

7. The method of claim 1, wherein the transplant population of pancreatic islet cells releases more insulin as compared to a control.

8. A method of preparing a pancreatic islet cell population for transplantation comprising the steps of
    administering an effective amount of a GDNF polypeptide having SEQ ID NO: 9 or variants with at least 80% sequence identity to SEQ ID NO: 9 to a transplant donor and
    isolating a pancreatic islet cell population from the donor.

9. The method of claim 8, further comprising culturing the isolated islet cell population with an effective amount of a GDNF polypeptide having SEQ ID NO: 9 or variants with at least 80% sequence identity to SEQ ID NO: 9.

10. The method of claim 8, further comprising culturing the isolated islet cell population with glial cells.

* * * * *